United States Patent [19]

Lee et al.

[11] Patent Number: 5,814,638

[45] Date of Patent: Sep. 29, 1998

[54] OPHTHALMIC FORMULATION FOR TREATING MYOPIA COMPRISING DOPAMINE AGONIST AND CYCLODEXTRIN

[75] Inventors: Yong-Hee Lee; Yun-Jeong Choi; Mi-Kyeong Seo; Chang-Ho Lee; In-Chull Kim, all of Daejeon, Rep. of Korea

[73] Assignee: LG Chemical Ltd., Seoul, Rep. of Korea

[21] Appl. No.: 724,808

[22] Filed: Oct. 2, 1996

[51] Int. Cl.⁶ .................................................. A61K 31/495
[52] U.S. Cl. ............................................. 514/255; 514/912
[58] Field of Search ...................... 514/255, 912

[56] References Cited

U.S. PATENT DOCUMENTS 4,727,064  2/1988  Pitha ........................................ 514/58

FOREIGN PATENT DOCUMENTS

| 8911854 | 12/1989 | WIPO . |
| 9422445 | 10/1994 | WIPO . |
| 9528930 | 11/1995 | WIPO . |
| 9616659 | 6/1996  | WIPO . |

OTHER PUBLICATIONS

WPIDS 003105 (1989)—Iuvone et al.
WPID33500 (1984).
T. Loftsson et al., PZ Wiss., vol. 136, No. 1, pp. 5–10 (1991).
J. Szejtli, Pharm. Tech. Int., vol. 3, No. 2, pp. 15–22 (1991).
O. Reer et al., J. Pharm. Sci., vol. 83, No. 9, pp. 1345–1349 (1994).
K. A. Freedman et al., Curr. Eye. Res., vol. 12, No. 7, pp. 641–647 (1993).

*Primary Examiner*—Zohreh Fay
*Attorney, Agent, or Firm*—Anderson, Kill & Olick, P.C.

[57] ABSTRACT

An ophthalmic formulation for treating myopia, which comprises a dopamine agonist and cyclodextrin or its derivative in combination with a pharmaceutically acceptable carrier.

8 Claims, 3 Drawing Sheets

OPHTHALMIC FORMULATION FOR TREATING MYOPIA COMPRISING DOPAMINE AGONIST AND CYCLODEXTRIN

FIELD OF THE INVENTION

The present invention relates to an ophthalmic formulation for treating myopia, which comprises a dopamine agonist and cyclodextrin or its derivative in combination with a pharmaceutically acceptable carrier.

BACKGROUND OF THE INVENTION

It has been estimated that about every fourth person on earth suffers from myopia and that about one-half or more of those are axial myopia caused by elongation of the eye along the visual axis. At birth, the human eye is about two-thirds the adult size and is relatively short in the axial direction. As a consequence, young children tend to be farsighted. As the eye grows during childhood, there occurs compensatory fine tuning of the optical properties of the cornea and lens to the increasing ocular length. Often the entire process takes place virtually flawlessly and the eye becomes emmetropic. When this fine tuning process fails, it usually brings about a lengthened eye. As a result, distant images get focused in front of the plane of the retina and axial myopia results(Josh Wallman, Retinal Control of Eye Growth and Refraction, *Progress in Retinal Research,* 12, 133–153(1993); and R. A. Stone et al., U.S. Pat. No. 5,284,843, filed on Apr. 10, 1991).

Hitherto, many theories have been put forth to explain the development of myopia. There is now a substantial evidence to link the function of the posterior part of the eye, especially image quality at the retina and hence the nervous system, to the postnatal regulation of ocular growth(R. A. Stone et al., Postnatal Control of Ocular Growth: Dopaminergic Mechanisms, Ciba Foundation Symposium 155, 45–62 (1990)). For example, there is an evidence that myopia develops in an eye when it is subjected to retinal image degradation; Josh Wallman has reported that axial myopia can be experimentally induced in either birds or primates, when the retina is deprived of formed images, e.g., by suturing eyelids(*Progress in Retinal Research,* 12, 133–153 (1993)). The experimental myopia induced in primates such as monkeys precisely mimics human axial myopia. Thus, the vision process is apparently involved in the feedback mechanism which regulates the postnatal ocular growth.

Retinal neurochemicals, i.e., neuro-active chemical compounds, are the essential elements in the vision process. Specifically, image-forming light is sensed by the light receptors, i.e., the rods and cones of the retina. These receptors act as transducers changing the light energy into electrical and/or chemical signals. In the normal process of transmitting the image information to the brain, retinal nerve cells, in association with the photo receptors, release neurochemicals to pass information to adjacent retinal cells as parts of a network in the retina leading to the optic nerve. In contrast, when a young bird or primate is deprived of normal images, chemical alterations take place in the retina concurrently with the excessive ocular growth leading to myopia. These chemical alterations include reduced retinal concentrations of the neurochemical dopamine, and its metabolite 3,4-dihydroxyphenylacetic acid(DOPAC) (R. A. Stone et al., *Proc. Natl. Acad. Sci. U.S.A.,* 86, 704–706(1989)).

Dopamine interacts with two major types of receptors, the D1 and D2 receptors. The D1 receptors are linked to the stimulation of adenylate cyclase in rat retina. The D2 receptors, however, are coupled negatively to adenylate cyclase. Apomorphine and pergolide are D1 and D2 agonists, and bromocriptine, lisuride, lergotrile, quinpirole, and CQ32-084 are D2 agonists.

It has been reported that the ocular administration of a dopamine agonist, e.g., apomorphine, or a dopamine antagonist, e.g., butyrophenone and haloperidol, to the eye of a young maturing animal can inhibit, and in some cases completely prevent, the axial enlargement of the eye subjected to conditions ordinarily leading to ocular enlargement (R. A. Stone et al., U.S. Pat. No. 5,284,843, filed on Apr. 10, 1991). Further, it has been reported that daily intravitreal injections of apomorphine block form-deprivation myopia (FDM) in young chickens(B. Rohrer et al., *Vis. Neurosci.,* 10, 447–453(1993)).

Various formulations of dopamine agonists have been investigated for their systemic therapeutic effects in treating Parkinsonism. U.S. Pat. No. 4,772,616(Daus et al., filed on Sep. 20, 1988) discloses a pharmaceutical composition containing pergolide, which is stabilized against the photo-decomposition by incorporating therein polyvinylpyrrolidone, alpha-tocopherol succinate, or propyl gallate. U.S. Pat. No. 4,929,640(Waddell et al., filed on May 29, 1990) discloses a pergolide composition which is stabilized against oxidation by incorporating therein a stabilizing agent selected from methionine, cysteine, and cysteine hydrochloride. It has been reported that apomorphine in water or plasma can be stabilized by the addition of anti-oxidants such as ascorbic acid and sodium bisulfate(Wilcox R. E. et al.,*J. Pharm. Sci.,* 69, 974–976(1980)), and that the stability of apomorphine is improved by the addition of 0.01% mercaptoethanol(E. Sam et al., *J. Chromatoqr.,* 658 (2), 311–317(1994)). Cabbat F. S. et al. have reported that dopamine and apomorphine are unstable in Tris buffer at pH 7.4, but their stabilities can be greatly enhanced by the addition of sodium acetate(*Res. Commun. Chem. Pathol. Pharmacol.,* 47, 333–343(1985)).

U.S. Pat. Nos. 4,501,749(Robinson et al., filed on Feb. 26, 1985) and 4,654,345(Thomas Cavanak et al., filed on Oct. 18, 1985) disclose stable ophthalmic formulations for treating glaucoma, which are lyophilizates comprising bromocriptine or an acid addition salt thereof capable of reconstituting in an isotonic vehicle. French patent publication No. 2 661 832(Corbiere, filed on Nov. 5, 1990) discloses a stable ophthalmic formulation which comprises bromocriptine, polyethylene glycol and serum. However, these formulations have the problem that because the pH values of the formulations range from about 3.5 to about 4.5, i.e., out of physiological pH range, it is difficult to employ those formulations for the ophthalmic administration. Moreover, dopamine agonists have poor water-solubilities at physiological pH.

Cyclodextrins are oligomers of glucose which are produced by the enzymatic degradation of starch by cyclodextrin transglycosylase. Cyclodextrins are classified by the number of α-1,4-linked glucose units which occur in their molecular structure. Alpha-cyclodextrin(α-CD) has six such units, β-cyclodextrin(β-CD) has seven, and γ-cyclodextrin (γ-CD), eight(K. Uekama, *Pharmaceutical Applications of Cyclodextrin Complexations, Yakugaku Zasshi,* 101, 857-(1981)). In these compounds, the C-1 chain conformation of the glucose monomers imparts to the molecule a cone-like structure in which the hydroxy groups are oriented on the exterior of the torus. The narrower end of the cone contains the primary hydroxy functionalities, while the wider face contains the secondary hydroxy groups. This arrangement makes the cyclodextrin exterior decidedly hydrophilic. The secondary hydroxy groups, can, however, interact via hydrogen bonding to stabilize the crystalline lattice. This reduces to a large extent the solubility of cyclodextrins, especially, β-CD, in water. Most importantly, the interior of the cyclodextrin cone is hydrophobic due to the presence of the skeletal carbons and ethereal oxygens which line the cavity. The result of this architecture is a lipoidal microenvironment which can solubilize non-polar compounds. Taken as a whole, cyclodextrins are water-soluble compounds which can form reversible complexes with poor water-soluble molecules resulting in a soluble molecular inclusion complex. The amphiphatic nature of cyclodextrins has been exploited to camouflage undesirable physicochemical properties of several pharmacologically active agents. One of the most important improvements afforded by complexation is an increase in water-solubility. Complexation of compounds can also stabilize chemically weak points in a molecular structure assuming that the sensitive portion of the molecule has penetrated into the cyclodextrin cavity. Chemically modified cyclodextrins such as 2-hydroxypropyl-β-cyclodextrin(HPCD) and sulfobutylether-β-cyclodextrin are amorphous isomeric mixtures which are potent complexing agents and innocuous when administered, i.e., either acutely or subchronically(M. E. Brewster et al.,*J. Parent. Sci. Tech.*, 43, 231–240(1989); M. E. Brewster et al., *Int. J. Pharmaceut.*, 59, 231–243(1990); V. J. Stella et al., *Int. J. Pharm.*, 120, 189–195(1995); and P. Jarho et al., *J. Pharm. Pharmacol.*).

For the purpose of inhibiting the abnormal postnatal axial growth of the eye, it is desirable to maximize the delivery of a therapeutic agent to the vitreous humour and retina, while minimizing systemic absorption of the agent to prevent possible systemic side effects. Generally, ocular absorption of a therapeutic agent into the posterior chamber of the eye, as opposed to its systemic absorption, depends not only on the relevant ocular anatomy and physiology, but also on the physicochemical property of the agent and the form of the ophthalmic formulation. Therefore, formulation techniques should be investigated not only for the improvement of in vitro physical stability and solubility, but also for the improvement of in vivo therapeutic efficacy by maximizing ocular absorption, while minimizing systemic absorption.

One such formulation technique is to prolong the residence time of a therapeutic agent applied in the conjunctival sac by employing a mucoadhesive, e.g., water-soluble polymers(Vincent H. L. Lee, *Precorneal, Corneal, and Postcorneal Factors in Ophthalmic Drug Delivery Systems*, 1993, by Marcel Dekker). Incorporation of 3.75% poly (vinyl alcohol) into an ophthalmic formulation afforded a 52-fold increase in the iris-ciliary body to plasma drug concentration ratio(Lee et al., *J. Ocular Pharmacol.*, 9, 47–58(1993)). Also, gentamicin penetration via the conjunctival-scleral pathway was facilitated by intensified contact between the mucoadhesive polymer, e.g., polycarbophil, and the underlying bulbar conjunctiva(Claus-Michael Lehr et al., *Invest. Ophthalmol. Vis. Sci.*, 35, 2809–2814(1994)).

However, no ophthalmic formulation containing a dopamine agonist has thus far been developed, primarily because of the stability and solubility problems of the dopamine agonist at physiological pH and, therefore, there has continued to exist a need to develop an ophthalmic formulation for treating myopia, which has an improved therapeutic efficacy at physiological pH.

SUMMARY OF THE INVENTION

Accordingly, it is a primary object of the present invention to provide an ophthalmic formulation for treating myopia, which has an improved therapeutic efficacy at physiological pH.

In accordance with the present invention, there is provided an ophthalmic formulation for treating myopia, which comprises a dopamine agonist and cyclodextrin or its derivative in combination with a pharmaceutically acceptable carrier.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1A:
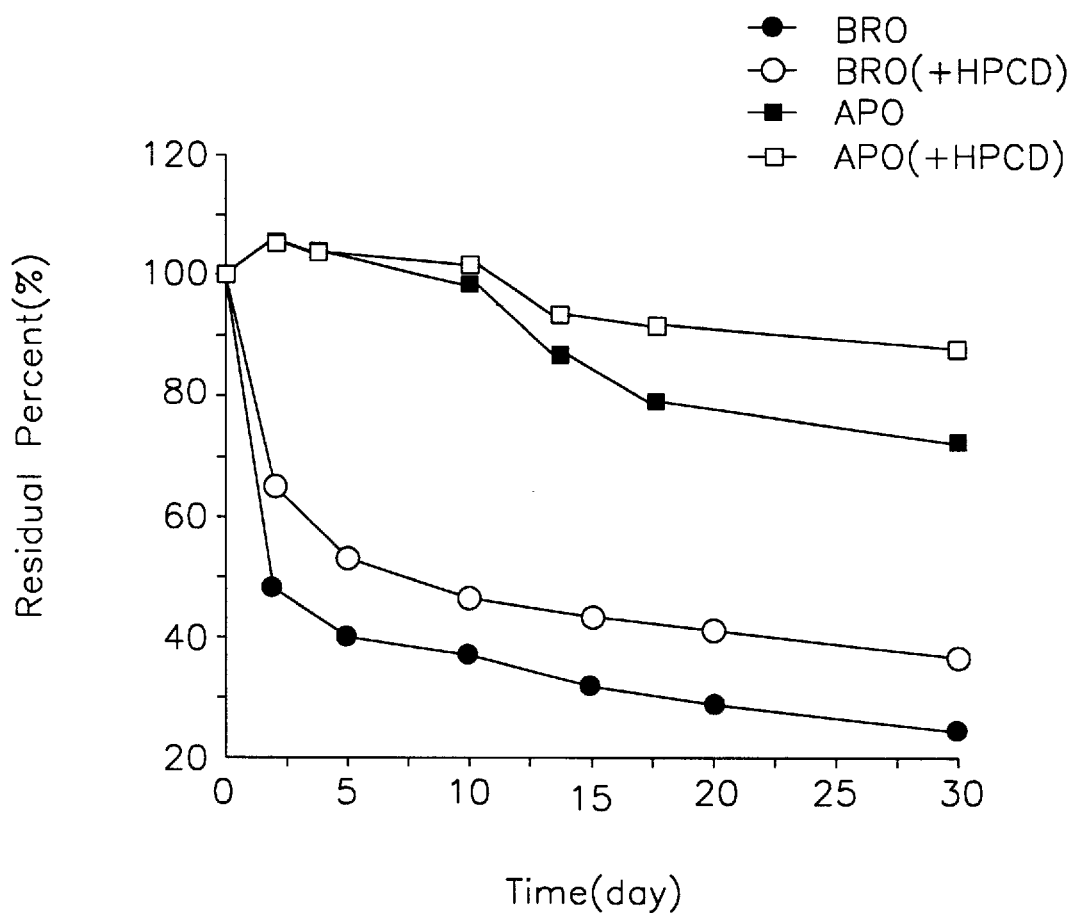
FIG. 1A shows the stabilities of bromocriptine and apomorphine at 25° C.

The ophthalmic formulation of the present invention for treating myopia comprises a dopamine agonist and cyclodextrin or its derivative in combination with a pharmaceutically acceptable carrier, and may further comprise a water-soluble polymer.

Examples of the dopamine agonist useful in the present invention include dopamine D1/D2 agonists and dopamine D2 agonists. The dopamine agonists are preferably selected from the group consisting of: bromocriptine, apomorphine, pergolide lisuride, lergotrile, quinpirole, and CQ32-084, wherein bromocriptine is most preferred.

The concentration of the dopamine agonist in the present formulation may range from 0.001 to 3%(w/v), preferably 0.005 to 2%(w/v). When bromocriptine is employed as the dopamine agonist, it may be preferably employed at a concentration ranging from 0.01 to 0.2%(w/v).

The ophthalmic formulation of the present invention may comprise cyclodextrin or its derivative at a concentration of 50%(w/v) or less, preferably 5 to 40%(w/v). Cyclodextrins which may be used in the present invention include alpha-cyclodextrin(α-CD), β-cyclodextrin(β-CD), and γ-cyclodextrin(γ-CD). Representative cyclodextrin derivatives that may be used in the present invention include 2-hydroxypropyl-β-cyclodextrin(HPCD), 2,3-dihydroxypropyl-β-cyclodextrin, 3-hydroxypropyl-β-cyclodextrin, dimethyl-β-cyclodextrin, 2-hydroxyethyl-β-cyclodextrin, trimethyl-β-cyclodextrin and sulfobutylether-β-cyclodextrin, wherein 2-hydroxypropyl-β-cyclodextrin is most preferred.

The present formulation may further comprise one or more water-soluble polymers to increase the viscosity of the formulation and the bioavailability of drug, and also to delay the washout of the formulation from the tear film. The water-soluble polymers can bind at the corneal and conjunctival surface, thereby increasing the drug retention time and stabilizing the tear film. Suitable water-soluble polymers that may be used in the present formulation include polyvinyl pyrrolidone(PVP), polyvinyl alcohol(PVA), hydroxypropyl cellulose(HPC), hydroxypropylmethylcellulose (HPMC), poloxamer 407, hyaluronic acid, and polycarbophil, wherein polyvinyl pyrrolidone, polyvinyl alcohol, hydroxypropyl cellulose and hyaluronic acid are preferred.

The concentration of the water-soluble polymer in the formulation may range 20%(w/v) or less, preferably, from 0.01 to 7%(w/v).

The ophthalmic formulation of the present invention may be prepared in accordance with any of the conventional procedures and it may be in the form of a solution, suspension, semi-solid or solid. The ophthalmic formulation may additionally include fillers, anti-agglutinating agents, lubricating agents, wetting agents, flavoring agents, emulsifiers, preservatives and the like. The formulation may be so prepared as to provide either quick, sustained or delayed release of the active ingredient after its administration to a patient, by employing any of the procedures well known in the art.

The pharmaceutical formulations can be administered via various routes including ocular instillation, subconjunctival administration, and intravitreal administration. A typical daily dose of the dopamine agonist may range 6 mg or less/whole body weight, preferably 4 mg or less/whole body weight, and can be administered in a single dose or in divided doses. However, it should be understood that the amount of the dopamine agonist actually administered ought to be determined in light of various relevant factors including the condition to be treated, the chosen route of administration, and the severity of the patient's symptom; and, therefore, the above dose should not be intended to limit the scope of the invention in any way.

The ophthalmic formulation of the present invention shows an improved in vitro stability and solubility and an improved in vivo therapeutic efficacy by maximizing ocular absorption of the active ingredient, while minimizing its systemic absorption at physiological pH.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1
Stability and Solubility of Dopamine Agonists

The stability and solubility of dopamine agonists, i.e., bromocriptine(BCT), apomorphine(APO), pergolide(PER), and lisuride(LIS) were tested as follows.

For the stability test, solutions each containing 100 $\mu$g/ml of the dopamine agonist in 10 mM citrate buffer(pH 5) were incubated at 25° C. for 30 days with or without added 2-hydroxypropyl-$\beta$-cyclodextrin(HPCD, average molar substitution=0.8, average molecular weight=1500; 20 wt % based on the solution). For the solubility test, solutions each containing 20 mg/ml of the dopamine agonist in 10 mM citrate buffer(pH 5) were incubated at 25° C. for 24 hours with or without added HPCD(20 wt % based on the solution) and filtered through a 0.45 $\mu$m filter.

The amounts of the dopamine agonists in sample solutions of the stability and solubility tests were determined by HPLC method with fluorescence detector.

Figure 1B:
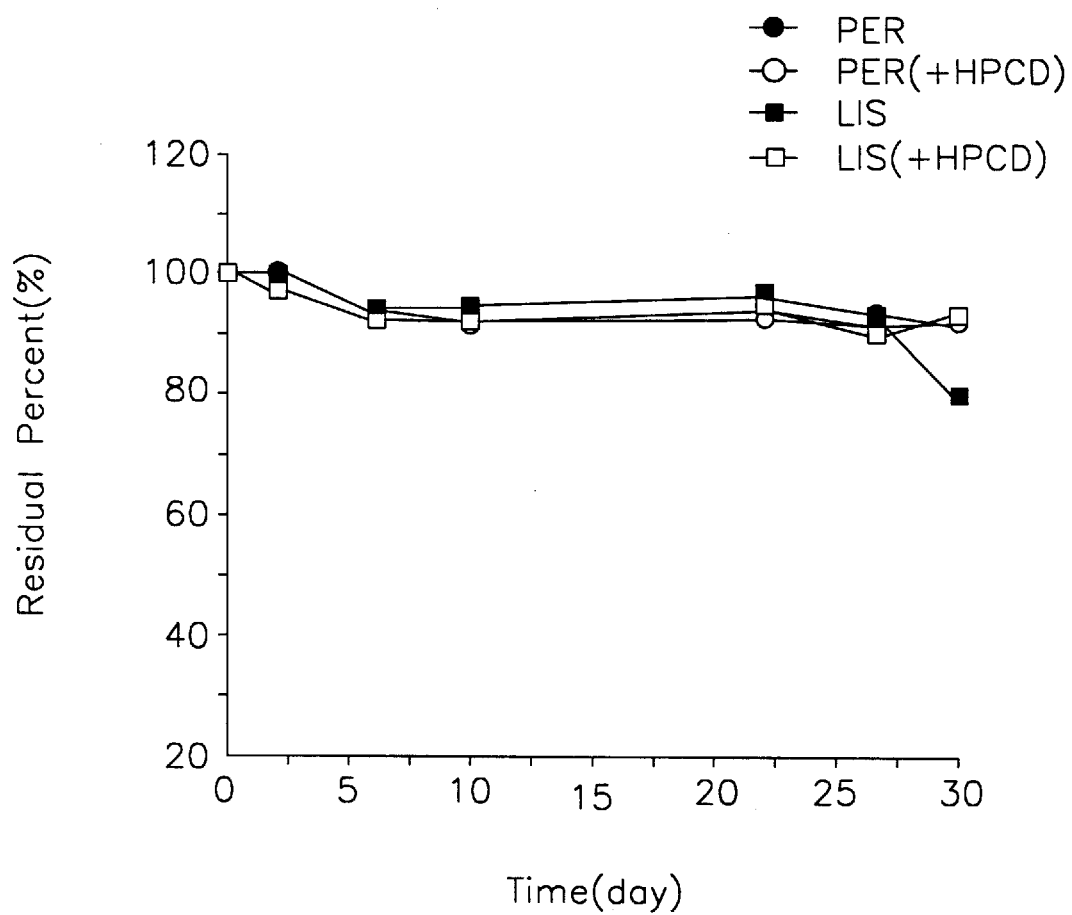
FIG. 1B depicts the stabilities of pergolide and lisuride at 25° C.
Figure 2:
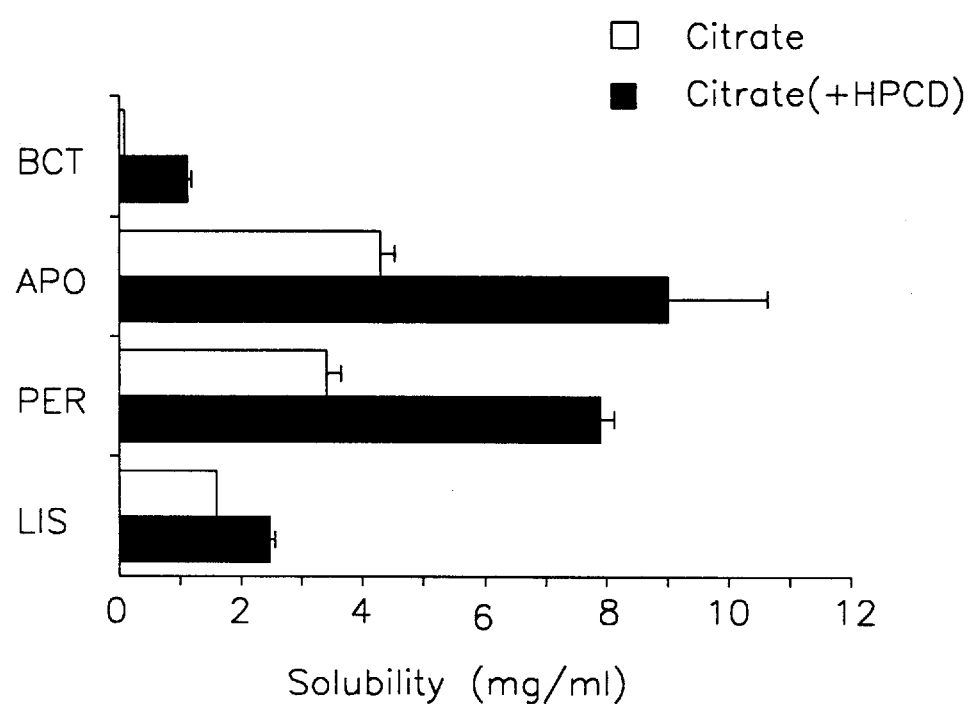
FIG. 2 compares the solubilities of bromocriptine, apomorphine, pergolide and lisuride at 25° C. in 10 mM citrate buffer(pH 5.0).

The results are shown in FIGS. 1A, 1B and 2. Each data point in FIGS. 1A and 1B represents the mean of two determinations and each value in FIG. 2 is the mean±SD (standard deviation) of three determinations. The presence of HPCD bring about significant increases in the stabilities of bromocriptine and apomorphine, while HPCD does not affect the stabilities of pergolide and lisuride. The addition of HPCD also bring about marked increases in the solubilities of the dopamine agonists; by a factor of 19 for bromocriptine, and two for apomorphine, pergolide, and lisuride.

Further, the stability of a solid state complex of bromocriptine and HPCD was tested by incubating two lyophilizates, each containing 0.2 mg or 1 mg of bromocriptine in 200 mg HPCD, at 25° C. and 40° C. for over 8 months. The bromocriptine in either of the lyophilizates remained unchanged over 8 months.

EXAMPLE 2
Ocular and Systemic Absorption of Bromocriptine

The amounts of bromocriptine absorbed via the ocular and systemic pathways were determined for the following ophthalmic formulations.

25 $\mu$l of an ocular formulation containing 0.1% bromocriptine(pH 5) in 2.2% glycerol(Formulation I), which was prepared in accordance with the method of Stone et al.(U.S. Pat. No. 5,284,843, filed on Apr. 10, 1991), and 25 $\mu$l of an ocular formulation containing 0.1% bromocriptine(pH 5) in 20% HPCD(Formulation II) were administered to the eyes of Newzealand white albino rabbits (Younam, Korea) via ocular instillation, respectively.

The amount of ocularly absorbed bromocriptine was measured at 120 and 240 min. after the ocular administration, while that absorbed into the systemic route was measured 2 hours after the ocular administration.

The amounts of bromocriptine entered into the ocular and systemic pathways were also determined after intravenously administering 50 $\mu$l of Formulation II to albino rabbits.

The results are shown in Tables I and II, wherein each value is the mean±SEM(standard error) of four determinations.

TABLE I

Eye tissue concentration of bromocriptine (ng/g or ml)

| | | Administration route | | |
|---|---|---|---|---|
| Time | | Ocular | | |
| after administration (min) | Eye tissue | Formulation I | Formulation II | Intravenous Formulation II |
| 120 | Cornea | 598.58 ± 185.50 | 3081.65 ± 426.12 | 0 |
| | Aqueous humour | 10.43 ± 1.01 | 37.54 ± 12.08 | 3.10 ± 1.80 |
| | Iris-ciliary body | 33.49 ± 10.65 | 82.29 ± 8.61 | 0 |
| | Vitreous humour | 0.29 ± 0.29 | 0.82 ± 0.22 | 0 |
| 240 | Cornea | 513.94 ± 113.21 | 814.13 ± 259.97 | 3.48 ± 3.48 |
| | Aqueous humour | 9.50 ± 1.35 | 17.46 ± 4.73 | 0 |
| | Iris-ciliary body | 11.92 ± 6.85 | 28.83 ± 5.25 | 0 |
| | Vitreous humour | 0.32 ± 0.22 | 1.26 ± 0.76 | 0 |

TABLE II

Plasma concentration of bromocriptine (ng/ml)

| | Administration route (Formulation II) | |
|---|---|---|
| Time (min) | Ocular | Intravenous |
| 1 | 0.80 ± 0.55 | 9.19 ± 1.65 |
| 3 | 0.76 ± 0.20 | 3.64 ± 0.19 |
| 6 | 1.45 ± 0.41 | 2.09 ± 0.08 |
| 10 | 1.52 ± 0.65 | 1.52 ± 0.18 |
| 15 | 1.87 ± 0.69 | 1.17 ± 0.24 |
| 20 | 1.63 ± 0.48 | 0.90 ± 0.18 |

TABLE II-continued

Plasma concentration of bromocriptine (ng/ml)

| Time (min) | Administration route (Formulation II) | |
|---|---|---|
| | Ocular | Intravenous |
| 30 | 1.42 ± 0.96 | 0.65 ± 0.15 |
| 45 | 0.46 ± 0.12 | 0.47 ± 0.03 |
| 60 | 0.26 ± 0.04 | 0.41 ± 0.01 |
| 90 | 0.11 ± 0.07 | 0.19 ± 0.02 |
| 120 | 0 | 0.09 ± 0.05 |

As can be seen from Tables I and II, Formulation II shows higher eye tissue concentration than Formulation I by a factor of 2 to 5. However, the eye tissue concentration of bromocriptine was negligible when Formulation II was administered intravenously. In the case when Formulation II was administered ocularly, the plasma bromocriptine concentration was lower than 2 ng/ml.

Therefore, it can be concluded that Formulation II, which comprises bromocriptine and HPCD, shows a high efficacy to deliver bromocriptine to the eye tissues, e.g., vitreous humour, when administered ocularly.

EXAMPLE 3

Effect of Water-Soluble Polymers on Absorption of Bromocriptine

The delivery of bromocriptine into the posterior chamber of eye through the ocular absorption pathway was investigated with various formulations containing bromocriptine, HPCD and a water-soluble polymer.

An ocular formulation containing 0.1% bromocriptine and 20% HPCD(Formulation I) and four ocular formulations each containing 0.1% bromocriptine, 20% HPCD and a water-soluble polymer selected from the group consisting of: 3.5% polyvinyl pyrrolidone(PVP, MW: 360,000) (Formulation II), 0.85% hydroxypropyl cellulose(HPC, MW: 370,000)(Formulation III), 2.2% polyvinyl alcohol (PVA, MW: 127,000)(Formulation IV), and 0.02% hyaluronic acid(HA, MW: 3 million)(Formulation V) were prepared. The formulations had a pH of 5.0 and a viscosity of 30±5 cps.

25 μl portions of the five formulations were administered to the eyes of albino rabbits via ocular instillation, and the ocular and systemic absorptions of bromocriptine were measured in accordance with the method described in Example 2. The results are shown in Tables III and IV, wherein each value is the mean±SEM of four determinations.

As can be seen from Tables III and IV, the eye tissue concentration of bromocriptine increased by the addition of the water-soluble polymers, while the systemic plasma concentrations of bromocriptine remained substantially unchanged. Further, addition of 3.5% PVP shows the highest efficacy in increasing the ocular absorption of bromocriptine.

TABLE III

Eye tissue concentration of bromocriptine (ng/g or ml)

| Time min | Eye tissue | Formulation | | | | |
|---|---|---|---|---|---|---|
| | | I | II | III | IV | V |
| 120 | Cornea | 3081.65 ± 426.12 | 5391.83 ± 1174.52 | 3937.73 ± 1011.44 | 5083.87 ± 761.20 | 3817.65 ± 321.48 |
| | Aqueous humour | 37.54 ± 12.08 | 54.45 ± 7.84 | 40.73 ± 3.99 | 49.91 ± 2.10 | 41.44 ± 13.92 |
| | Iris-ciliary body | 82.29 ± 8.61 | 184.32 ± 39.46 | 121.35 ± 34.11 | 158.23 ± 45.58 | 159.01 ± 31.90 |
| | Vitreous humour | 0.82 ± 0.22 | 3.50 ± 0.91 | 1.56 ± 0.56 | 2.15 ± 0.85 | 1.58 ± 0.92 |
| 240 | Cornea | 814.13 ± 259.97 | 3039.48 ± 509.51 | 2293.15 ± 127.45 | 2030.99 ± 614.79 | 1474.67 ± 255.25 |
| | Aqueous humour | 17.46 ± 4.73 | 44.29 ± 3.61 | 23.75 ± 2.34 | 22.76 ± 7.51 | 14.18 ± 2.19 |
| | Iris-ciliary body | 28.83 ± 5.25 | 134.67 ± 28.51 | 116.81 ± 24.35 | 63.85 ± 10.83 | 73.21 ± 16.10 |
| | Vitreous humour | 1.26 ± 0.76 | 1.94 ± 0.41 | 1.08 ± 0.47 | 0.71 ± 0.16 | 0.81 ± 0.34 |

TABLE IV

Plasma Concentration of bromocriptine (ng/ml)

| Time (min) | Formulation | | | | |
|---|---|---|---|---|---|
| | I | II | III | IV | V |
| 1 | 0.80 ± 0.55 | | | | |
| 2 | | 0.35 ± 0.21 | 0.50 ± 0.20 | 0.56 ± 0.23 | 0.62 ± 0.02 |
| 3 | 0.76 ± 0.20 | | | | |
| 5 | | 2.48 ± 1.09 | 1.46 ± 0.19 | 1.67 ± 0.47 | 1.21 ± 0.12 |
| 6 | 1.45 ± 0.41 | | | | |
| 10 | 1.52 ± 0.65 | 1.66 ± 0.34 | 2.34 ± 0.50 | 2.34 ± 0.32 | 1.79 ± 0.23 |
| 15 | 1.87 ± 0.69 | | | | |
| 20 | 1.63 ± 0.48 | 2.71 ± 1.04 | 1.63 ± 0.16 | 1.75 ± 0.20 | 1.12 ± 0.11 |
| 30 | 1.42 ± 0.96 | 1.50 ± 0.49 | 1.24 ± 0.18 | 1.12 ± 0.07 | 0.77 ± 0.08 |
| 45 | 0.46 ± 0.12 | 0.85 ± 0.18 | 0.65 ± 0.11 | 0.62 ± 0.07 | 0.55 ± 0.12 |
| 60 | 0.26 ± 0.04 | 0.41 ± 0.06 | 0.48 ± 0.11 | 0.43 ± 0.05 | 0.28 ± 0.02 |
| 90 | 0.11 ± 0.07 | 0.28 ± 0.12 | 0.27 ± 0.04 | 0.19 ± 0.08 | 0.13 ± 0.08 |
| 120 | 0 | 0.12 ± 0.08 | 0.04 ± 0.04 | 0 | 0 |

EXAMPLE 4

To test the inhibitory effect of bromocriptine on the axial length prolongation of the eye, experimental axial myopia was induced in chicks by suturing their right eyelids in accordance with the method of Wallman (*Progress in Retinal Research*, 12, 133–153(1993)).

Three ocular formulations each containing 0%(Formulation I), 0.02%(Formulation II) or 0.1% (Formulation III) of bromocriptine, 20% HPCD and 3.5% PVP(MW: 360,000) were prepared and 100 μl portions thereof were applied to the sutured eyes of chicks twice a day for 28 days. Then, the axial length of the eyeballs was measured and the results are shown in Table V, wherein each value is the mean±SD of 10 determinations. The ophthalmic formulations II and III, which contain 0.02% and 0.1% of bromocriptine, respectively, showed significant inhibitory effects on the axial length growth.

TABLE V

Axial length (mm) of eyeballs after administration of bromocriptine formulations

| Formulation | Occluded eyes | Non-occluded eyes |
|---|---|---|
| I | 11.39 ± 0.27 | 10.61 ± 0.15 |
| II | 11.20 ± 0.40 | 10.54 ± 0.28 |
| III | 11.26 ± 0.38 | 10.52 ± 0.33 |

While the invention has been described with respect to the above specific embodiments, it should be recognized that various modifications and changes may be made to the invention by those skilled in the art which also fall within the scope of the invention as defined by the appended claims.

What is claimed is:

1. An ophthalmic formulation for treating myopia, which comprises bromocriptine and cyclodextrin or its derivative in combination with a pharmaceutically acceptable carrier.

2. The ophthalmic formulation of claim 1, wherein the concentration of bromocriptine is 0.01 to 0.2%(w/v).

3. The ophthalmic formulation of claim 1, wherein the concentration of cyclodextrin or its derivative is 5 to 40% (w/v).

4. The ophthalmic formulation of claim 1, wherein the cyclodextrin derivative is 2-hydroxypropyl-β-cyclodextrin.

5. The ophthalmic formulation of claim 1, which further comprises a water-soluble polymer.

6. The ophthalmic formulation of claim 5, wherein the water-soluble polymer is selected from the group consisting of polyvinyl pyrrolidone, polyvinyl alcohol, hydroxypropyl cellulose, and hyaluronic acid.

7. The ophthalmic formulation of claim 5, wherein the concentration of the water-soluble polymer is 0.01 to 7%(w/v).

8. A method for controlling an abnormal postnatal growth of the eye of a maturing animal, which comprises administering ocularly an effective amount of the ophthalmic formulation according to any one of claims 1 and 2 to 7 to the animal.

* * * * *